United States Patent
Carmi

(10) Patent No.: US 9,905,044 B1
(45) Date of Patent: Feb. 27, 2018

(54) SYSTEMS AND METHODS FOR FUNCTIONAL IMAGING

(71) Applicant: GENERAL ELECTRIC COMPANY, Schenectady, NY (US)

(72) Inventor: Raz Carmi, Haifa (IL)

(73) Assignee: General Electric Company, Schenectady, NY (US)

( * ) Notice: Subject to any disclaimer, the term of this patent is extended or adjusted under 35 U.S.C. 154(b) by 70 days.

(21) Appl. No.: 15/247,592

(22) Filed: Aug. 25, 2016

(51) Int. Cl.
G06K 9/00 (2006.01)
G06T 15/08 (2011.01)
G06T 7/00 (2017.01)

(52) U.S. Cl.
CPC ............ *G06T 15/08* (2013.01); *G06T 7/0012* (2013.01)

(58) Field of Classification Search
CPC .................. H04N 5/367; G06T 7/0012; G06T 2207/10081; G06T 2207/10088; G06T 2207/10072; G06T 2207/10104; G06T 11/008; G06T 2207/20128; G06T 2207/30016; G06T 2207/30068; G06T 2207/30204; G06T 7/33; G06T 2207/10108; G06T 2207/20036; A61B 6/037; A61B 6/469; A61B 6/481; A61B 8/13
See application file for complete search history.

(56) References Cited

U.S. PATENT DOCUMENTS

| | | | |
|---|---|---|---|
| 6,728,424 B1 | 4/2004 | Zhu et al. | |
| 6,740,883 B1 | 5/2004 | Stodilka et al. | |
| 6,878,941 B2 | 4/2005 | Balan et al. | |
| 7,324,842 B2* | 1/2008 | Dale | A61B 5/055 382/128 |
| 7,348,564 B2 | 3/2008 | Wollenweber et al. | |
| 7,822,241 B2* | 10/2010 | Eck | A61B 6/12 382/128 |
| 8,423,118 B2* | 4/2013 | Wenzel | G06T 7/0012 382/128 |

(Continued)

FOREIGN PATENT DOCUMENTS

NL   2009138898   11/2009

*Primary Examiner* — Aaron W Carter
*Assistant Examiner* — Ian Lemieux
(74) *Attorney, Agent, or Firm* — Dean D. Small; The Small Patent Law Group, LLC

(57) ABSTRACT

A system includes a structural imaging acquisition unit, a functional imaging acquisition unit, and one or more processors. The structural imaging acquisition unit is configured to perform a structural scan to acquire structural imaging information of a patient. The functional imaging acquisition unit is configured to perform a functional scan to acquire functional imaging information of a patient. The one or more processors are configured to obtain, using the structural imaging information, a structural image of the patient including anatomical volumetric data; determine an anatomical probability map corresponding to a probability that a determined anatomical object correlates to potential functional data; obtain, using the functional imaging information, a functional image of the patient including functional volumetric data; re-distribute the functional volumetric data using the anatomical probability map to provide re-distributed functional volumetric data; and generate an image using the re-distributed functional volumetric data.

20 Claims, 7 Drawing Sheets

(56) References Cited

U.S. PATENT DOCUMENTS

| | | | |
|---|---|---|---|
| 8,447,090 B2 * | 5/2013 | Wakai | G06F 19/321 |
| | | | 382/131 |
| 9,532,762 B2 * | 1/2017 | Cho | A61B 6/502 |
| 9,730,663 B2 * | 8/2017 | Koehler | A61B 6/5258 |
| 9,818,191 B2 * | 11/2017 | Magda | G06T 7/0014 |
| 2003/0004405 A1 | 1/2003 | Townsend et al. | |
| 2003/0216631 A1 | 11/2003 | Bloch et al. | |
| 2004/0071325 A1 | 4/2004 | Declerck et al. | |
| 2005/0226527 A1 | 10/2005 | Weese et al. | |
| 2007/0258908 A1 | 11/2007 | Lanza et al. | |
| 2008/0009698 A1 * | 1/2008 | Boese | A61B 6/481 |
| | | | 600/407 |
| 2008/0064949 A1 | 3/2008 | Hertel et al. | |
| 2008/0095414 A1 | 4/2008 | Desh et al. | |
| 2008/0123922 A1 | 5/2008 | Gielen et al. | |
| 2009/0202125 A1 | 8/2009 | Zhao et al. | |
| 2012/0099770 A1 * | 4/2012 | Cagnan | A61B 19/50 |
| | | | 382/128 |
| 2016/0300343 A1 * | 10/2016 | Gazit | G06T 7/11 |
| 2017/0287175 A1 * | 10/2017 | Lin | G06T 11/008 |
| 2017/0323177 A1 * | 11/2017 | Sauer | G06K 9/6218 |

\* cited by examiner

SYSTEMS AND METHODS FOR FUNCTIONAL IMAGING

BACKGROUND OF THE INVENTION

The subject matter disclosed herein relates generally to systems and methods for imaging (e.g., diagnostic imaging of a patient).

Multi-modality imaging may be used to acquire both functional and structural imaging information. In conventional multi-modality systems, however, structural accuracy of the functional information may be insufficient. For example, the accuracy or resolution of the functional information may not be sufficient for reliable clinical usage.

BRIEF DESCRIPTION OF THE INVENTION

In one embodiment, a system is provided that includes a structural imaging acquisition unit, a functional imaging acquisition unit, and one or more processors. The structural imaging acquisition unit is configured to perform a structural scan to acquire structural imaging information of a patient. The functional imaging acquisition unit is configured to perform a functional scan to acquire functional imaging information of a patient. The one or more processors are configured to obtain, using the structural imaging information, a structural image of the patient including anatomical volumetric data; determine an anatomical probability map corresponding to a probability that a determined anatomical object correlates to potential functional data; obtain, using the functional imaging information, a functional image of the patient including functional volumetric data; re-distribute the functional volumetric data using the anatomical probability map to provide re-distributed functional volumetric data; and generate an image using the re-distributed functional volumetric data.

In another embodiment, a method is provided. The method includes obtaining a structural image of the patient including anatomical volumetric data. The method also includes determining an anatomical probability map corresponding to a probability that a determined anatomical object correlates to potential functional data. Further, the method includes obtaining a functional image of the patient including functional volumetric data. Also, the method includes re-distributing the functional volumetric data using the anatomical probability map to provide re-distributed functional volumetric data, and generating an image using the re-distributed functional volumetric data.

In another embodiment, a tangible and non-transitory computer readable medium is provided. The tangible and non-transitory computer readable medium includes one or more computer software modules configured to direct one or more processors. The tangible and non-transitory computer readable medium is configured to direct the one or more processors to: determine a first ratio based on functional image data for a given voxel and a neighboring voxel; determine a second ratio based on values of the anatomical probability map for the given voxel and the neighboring voxel; determine a local conditional expectation value based on the first and second ratios; and determine whether or not to re-distribute a portion of the functional volumetric data corresponding to the voxel based on the local conditional expectation value.

DETAILED DESCRIPTION OF THE INVENTION

Figure 1:
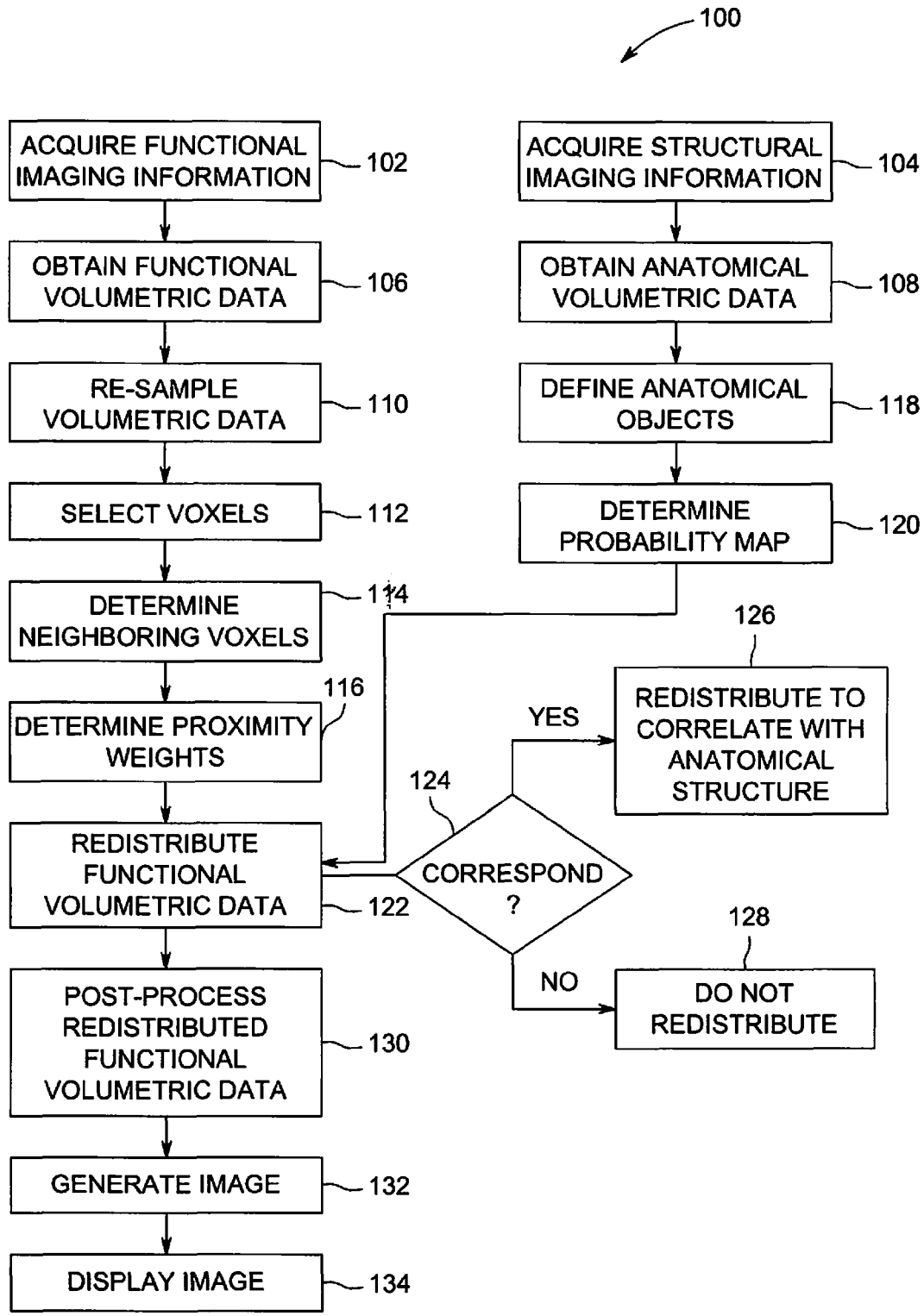
FIG. 1 is a flowchart of a method in accordance with various embodiments described herein.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for improving functional imaging data such as SPECT or PET in multi-modality imaging systems, based on corresponding anatomical imaging data such as CT or MRI. In various embodiments, functional volumetric image values are redistributed based on accurate assessment of distribution weights. The weights are based, on one hand, on a priori information such as the estimated targeting of the functional tracer to specific anatomical object, system spatial resolution, and probabilistic models. The weights are also based on local conditional analysis of functional imaging data distribution patterns with respect to the modeled spatial probabilities. Various embodiments provide for the preservation of functional data concentrations which are not originated from anatomical objects.

Various embodiments provide systems and methods for reforming functional data. In various embodiments, functional image data is obtained, and anatomical image data corresponding to the functional image data is also obtained. A probability map corresponding to determined anatomical object in the anatomical image data is also defined. The probability map models the potential of anatomical objects to express functional data signals observed in the functional image data. A set of local conditional expectations are then calculated based on the functional image data and the probability map. The local conditional expectations reflect the expectation levels that functional information is essentially originated from anatomical objects. Next, reformed functional image data is generated by redistributing the functional image data based on the set of local conditional expectations.

A technical effect of various embodiments described herein includes improved diagnostic imaging. A technical effect of various embodiments includes improved resolution of functional imaging information. A technical effect of various embodiments includes improved correlation between functional and anatomical images.

FIG. 1 illustrates a flowchart of a method 100 (e.g., a method for medical imaging). The operations of FIG. 1 may be implemented by one or more processors executing program instructions stored in memory. The method 100, for example, may employ structures or aspects of various embodiments (e.g., systems and/or methods) discussed herein, such as the system 500 (see FIG. 5 and related discussion). In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 100 may be used as one or more algorithms to direct hardware to perform one or more operations described herein. It should be noted, other methods may be used, in accordance with embodiments herein.

Before addressing the individual depicted steps of the example method 100, a general overview is provided. First, functional and anatomical volumetric image data are obtained. For example, the functional and anatomical volumetric image data may be obtained after tomographic reconstructions of acquired signals for the specific functional and anatomical modality systems. Generally, anatomical imaging modality systems as used herein may be used to image structures (e.g., bone, brain, tissue) of an object (e.g., human patient) being scanned, while functional imaging modalities may be used to image function (e.g., uptake of a radiotracer or other agent) of the object. Examples of functional imaging modality systems include positron emission tomography (PET), single photon emission computed tomography (SPECT), or nuclear medicine (NM) imaging, as well as magneto-encephalography (MEG) or electric-encephalography (EEG), for example. Examples of structural imaging modality systems include x-ray, computed tomography (CT), magnetic resonance imaging (MRI), and ultrasound (US). The functional volumetric image data may be referred to as a functional image volume and the anatomical volumetric image data may be referred to as an anatomical image volume. The functional and anatomical image volumes in various embodiments are co-registered and/or resampled to obtain a convenient shared voxel grid for mutual processing. It may be noted that co-registration may be satisfied up to reasonable deviation errors (e.g., no more than several millimeters). For example, the functional image volume may be re-sampled to match the voxel grid of the anatomical image volume. It may be noted that in various embodiments, the same acquisition system may be used to provide both the functional and structural imaging information used as discussed herein. For example, unique targeted CT or MRI contrast materials may be utilized, and the CT or MRI images may also provide functional information in addition to structural information. In some embodiments, other types of functional imaging information may be obtained by using techniques such as dynamic-CT, dynamic-MRI, spectral-CT, or functional-MRI, for example.

Before starting the image reformation processing (e.g., the process of adjusting one or more portions of the functional image volume to match one or more portions of the anatomical image volume), a set of analyzed voxels in the functional image volume and a corresponding set of neighbor voxels for each analyzed voxel are determined. For example, the set of analyzed voxels may refer to the whole functional image volume, or alternatively, to a smaller sub-set of the entire functional image volume. For instance, the set of analyzed voxels may be for a specific pre-determined segmented organ or tissue type, or, as another example, may be based on a threshold for a minimal considered image value in the functional image data. The set of neighbor voxels may be determined, for example, as those voxels within a sphere with a defined radius around the analyzed voxel. The radius of the sphere may be constant or varied, for example according to the estimated spatial resolution of the functional modality system. It may be noted that the radius may be different in different locations of the reconstructed field of view. In some embodiments, with respect to the neighbor voxels, a spatial weight distribution, or proximity weights, may be determined. The weights may be used to assign stronger correspondence where a neighbor voxel is closer to the analyzed voxel. For example, the weights may be determined as a 3D Gaussian function centered on the analyzed voxel.

The anatomical data may be used as part of two processes. In the first process, preferred anatomical objects may be defined, for example based on the targeted clinical application and an a priori knowledge about the targeting properties of the tracer or agent used for the corresponding functional imaging. For example, in an example scenario of imaging related to diseases related to bones, the skeleton and bones may be segmented (sharply or softly) based on known image value ranges and/or structural models and priors. As another example, specific brain tissue, or tumor tissue, or a whole organ may be segmented. Further, in some embodiments, several different tissue types or organs may be segmented, such as the hard (cortical) bones and soft (trabecular) bones of the skeleton. Further still, in some embodiments, smoothed transition values or weights between different object types may be generated. Such smoothing may be beneficial, for example, where anatomical data itself may suffer from inaccuracies such as image noise or artifacts.

In the second process using the anatomical data, a probability map is defined based on the previous determination of anatomical objects. The probability map is based on a predefined model regarding the probability that the determined anatomical objects may express functional data signals (e.g., the probability that an anatomical object is represented in the functional image volume). As one example, in bone-related disease imaging applications, bones are more likely than soft tissue to express functional data signals. Accordingly, the segmented bones may be assigned a higher probability value than soft tissue. For example, the segmented bones may receive a probability value of 0.8 (out of a maximum 1.0), and other adjacent soft tissues may receive a probability value of 0.2 (out of a maximum 1.0). The values for various tissues or structures may be set to reflect the clinical reality that there is still a chance that functional imaging tracer will concentrate outside of the bones. It may be noted that the previously mentioned values are provided by way of example; other structures and/or probability value settings may be employed in other embodiments. For example, hard bone may receive a 0.6 probability value, soft bone may receive a 0.3 probability value, and soft tissue may receive a 0.1 probability value. It may further be noted that, in some embodiments, the probability map values may be spatially smoothed between different segments.

With the anatomical probability map prepared, and the set of voxels in the functional image volume determined, one or more portions of the functional image may be re-distributed to improve image quality. Generally, all voxels to be analyzed may be processed, and functional image values are re-distributed across neighbor voxels to obtain reformed functional volumetric image data. The reformed or re-distributed functional data reflects calculated expectation levels that the functional information is essentially originated from the determined anatomical objects. The expectation levels may be determined locally based on several conditions and mathematical functions which include one or more aspects discussed herein. Accordingly, functional information having a higher correspondence (or likelihood of correspondence) with a particular structure may be re-distributed to better match, align with, or correspond to the location of the structure, and functional information having a lower correspondence (or likelihood of correspondence) with the particular structure may be unmodified from a previous location. Overall, it is likely that the quantitative accuracy of the functional information will be also improved in the re-distribution process. Additionally, the resulting re-distributed functional data may be re-sampled, for example to fit desired visual optimization or further processing. The final data is visualized (e.g., presented on a screen or print-out for a user). Optionally, the re-distributed final data may be presented visually with the original functional data and/or anatomical data. User confidence analysis of the image reformation results may also be provided. With a general overview having been provided, particular steps of the illustrated example are now discussed. It may be noted that one or more aspects discussed above (and/or variations thereof) may be utilized in one or more steps of the example method discussed below.

At 102, functional imaging information is acquired. For example, functional imaging information of a patient (or portion thereof) may be acquired using an imaging acquisition unit (e.g., functional imaging acquisition unit 530). The functional imaging acquisition unit, for example, may be configured to acquire one or more of PET or SPECT imaging information.

At 104, structural imaging information is acquired. For example, structural imaging information of a patient (or portion thereof) may be acquired using a structural imaging acquisition unit (e.g., structural imaging acquisition unit 510). The structural imaging acquisition unit, for example, may be configured to acquire one or more of CT, MRI, or US imaging information.

At 106, functional volumetric data is obtained. For example, a functional image may be reconstructed using the functional imaging data acquired at 102, with the functional image including the functional volumetric data. It may be noted that the functional volumetric data may refer in various embodiments to the entirety of the functional image, or just to a portion of the functional image. For example, the functional volumetric data may correspond to a volume of interest within the functional image.

At 108, anatomical volumetric data is obtained. For example, a structural image may be reconstructed using the structural imaging data acquired at 104, with the structural image including the anatomical volumetric data. It may be noted that the anatomical volumetric data may refer in various embodiments to the entirety of the structural image, or just to a portion of the structural image. For example, the anatomical volumetric data may correspond to a volume of interest within the structural image. In various embodiments, the structural image (and/or the anatomical volumetric data) and the functional image (and/or the functional volumetric data) may be co-registered with each other. In some embodiments, one or more of the functional volumetric data or the structural volumetric data may be resampled.

For example, in the illustrated embodiment, at 110, volumetric data is resampled. For example, the anatomical volumetric data obtained at 108 and/or the functional volumetric data obtained at 106 may be resampled to obtain volumetric voxel grids, with the voxel grids of the anatomical volumetric data and the voxel grids of the functional volumetric data matching each other.

At 112, a set of voxels to be analyzed for redistribution is selected. The set of voxels is selected from the functional volumetric data. In some embodiments, the set of voxels may be for the entire functional image. In some embodiments, the set of voxels may be for a portion of the functional image, for example of one or more volumes of interest. The set of voxels may be selected by an operator (e.g., an operator viewing the functional image on a screen and using a user interface to indicate a volume of interest). In some embodiments, the set of voxels may be selected automatically or autonomously, for example, based on a clinical task or diagnostic purpose of the imaging.

At 114, a set of neighboring voxels is determined for each voxel to be analyzed. For example, for each voxel of the volume of interest, a set of neighboring voxels is selected. In some embodiments, one or more neighboring voxels may be located outside of the volume of interest. As discussed herein, in some embodiments, the neighboring voxels may include voxels that are not immediately adjacent to the particular voxel being analyzed. For example, a sphere with a defined radius centered about the particular voxel to be analyzed may be used to define the set of neighboring voxels for the particular voxel. It may be noted that, in some embodiments, the radius may be different in different locations of the functional volumetric data.

At 116, proximity weights are determined. For example, proximity weights for each of the neighboring voxel for a particular voxel to be analyzed may be determined based on a function of spatial distance and the position in the analyzed image volume. As discussed herein, in some embodiments, the weights may be determined as a 3D Gaussian function centered on the voxel to be analyzed.

At 118, preferred anatomical objects are defined. The preferred anatomical objects are defined within the anatomical volumetric data. For example, image voxel value ranges and/or structural segments corresponding to the volume of interest of the functional image may be defined. The particular voxel value ranges and/or structural segments may be defined based on the clinical application, as well as a priori knowledge about the target properties of a functional indicator (such as a radiotracer) used in conjunction with the functional imaging. As discussed herein, as one example, for clinical applications related to bone diseases, bones of interest may be segmented.

At 120, a probability map is determined. The probability map corresponds to the probability that a determined anatomical object correlates to potential functional data. The probability map may be based on a predefined model regarding the probability that a determined anatomical object or portion thereof (e.g., an anatomical object defined at 118) may express functional data signals. For example, for an example scenario using a radiotracer that tends to concentrate in bones, voxels of the anatomical volumetric data corresponding to bone locations may be assigned higher probability values than voxels that correspond to soft tissue locations.

At 122, functional volumetric data is redistributed. The functional volumetric data is redistributed using the anatomical probability map to provide re-distributed functional volumetric data. Generally, in various embodiments, if it is determined that the functional volumetric data corresponds to an anatomical structure using the anatomical probability map, the functional volumetric data is redistributed to align or correspond with the anatomical structure. It may be noted that the re-distribution may be determined and/or performed for a given voxel in a distributed manner among plural neighboring voxels. In some embodiments, for each analyzed voxel, the functional image values are redistributed across neighbor voxels to obtain the redistributed or reformed function volumetric image data. The reformed functional volumetric image data reflects the expectation with respect to local conditions (e.g., whether or not a pertinent structure is locally disposed) whether or not the functional information is essentially originated from determined anatomical objects.

Figure 2:
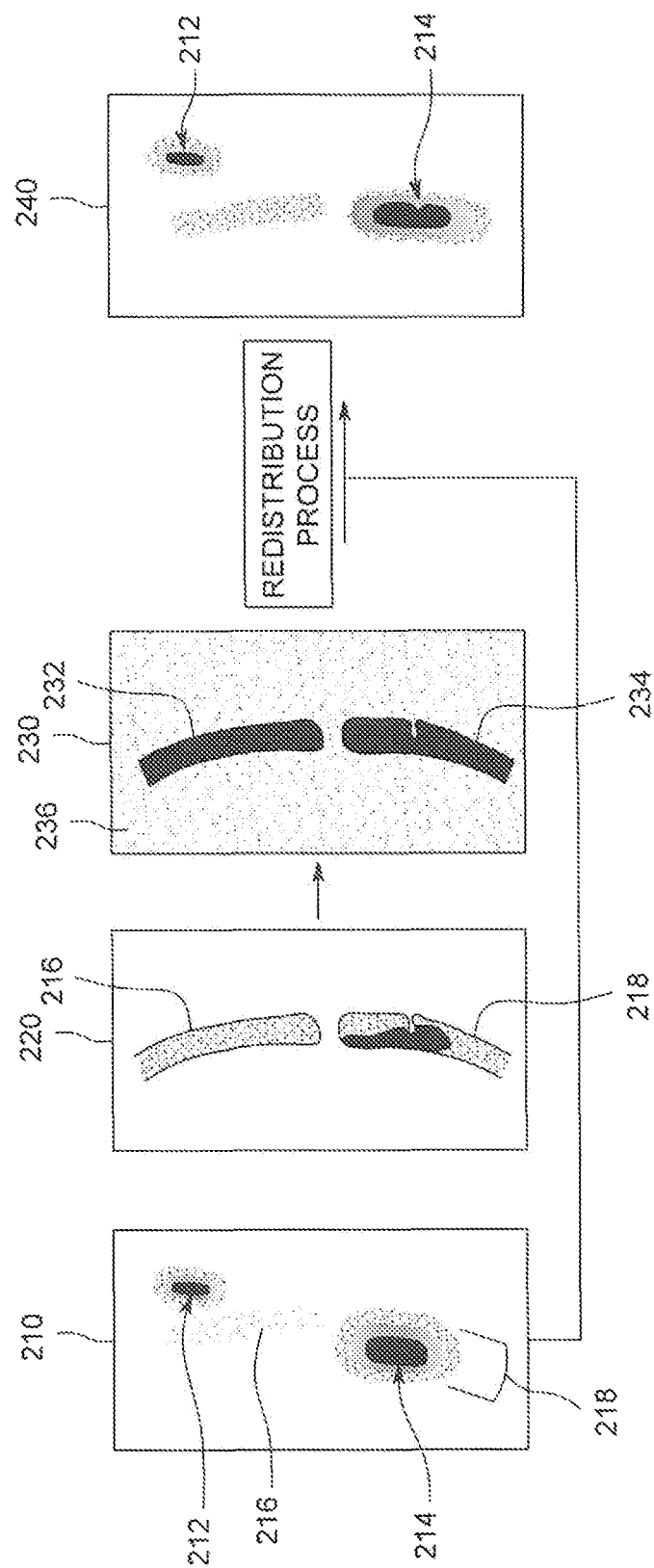
FIG. 2 is a schematic depiction of redistributing functional imaging information in accordance with various embodiments described herein.

The redistribution of functional volumetric data is depicted schematically in FIG. 2. As seen in FIG. 2, a functional image 210 and an anatomical image 220 are used to generate a new (or redistributed) functional image 240. Two functional signals are present in the functional image 210—namely, a first functional signal 212 and a second functional signal 214. As seen in FIG. 2, the first functional signal 212 does not originate from a bone structure 216; however, the second functional signal 214 originates from a bone structure 218.

The bone structure 216 and bone structure 218 are shown in the anatomical image 220 of FIG. 2 as well. The anatomical image 220 is used to generate the probability map 230. As seen in FIG. 2, the probability map 230 has three regions—a first region 232 corresponding to the bone structure 216, a second region 234 corresponding to the bone structure 218, and a third region 236 corresponding to soft tissue surrounding the bone structures. For example, for a scanning process using a radiotracer configured for analyzing bone, the first region 232 and second region 234 (which correspond to bone) may be assigned a probability of 0.8 and the third region 236 (which corresponds to soft tissue) may be assigned a probability of 0.2. Using the probability map 230, imaging data of the functional image 210 is redistributed to provide the new functional image 240. In the new functional image 240, the second functional signal 214, which corresponded to the bone structure 218, has been redistributed in accordance with the correlated bone structure 218 to more closely match or align with the correlated bone structure 218. Also, the quantitative accuracy of the functional signal 214 may be improved due to the increased functional values owing to the normalization in the re-distribution process (i.e., the mean functional quantity becomes more concentrated). However, the first functional signal 212, which did not correspond with a bone structure, is left intact in the new functional image 240 as seen in FIG. 2. Additional details regarding further examples of volumetric image redistribution are discussed in connection with method 300 and method 400. (See FIGS. 3 and 4 and related discussion).

Returning to FIG. 1, in the illustrated embodiment, at 124, it is determined if one or more portions of the functional volumetric data correspond to an anatomical structure. The anatomical probability map is used to make the determination. If it is determined that the one or more portions of the functional volumetric data correspond to the anatomical structure, at 126, the one or more portions of the functional volumetric data are redistributed to correlate with one or more portions of the anatomical volumetric data corresponding to the anatomical structure. For example, the functional volumetric data may be redistributed to more closely align with the pertinent anatomical structure. If, however, it is determined that the one or more portions of the function volumetric data do not correspond to the anatomical structure, at 128, the one or more portions of the functional volumetric data are not redistributed. Instead, the one or more portions may be left intact, unaltered, or unmodified, for example. Accordingly, functional information that is caused by or relates to a given structure is reformulated or redistributed to better align with the structure for improved image quality; however, functional information that is not caused by or does not relate to an anatomical structure is left in an original condition or not altered based on one or more anatomical structures in an imaging volume. It may be noted that, in the way the re-distribution is calculated and performed, the attempt to not redistribute one or more portions of the functional volumetric data may be replaced by a moderate redistribution instead of not distributing at all. The moderate redistribution may be effectively nulled by appended redistributions from other voxels or by the weighting with the functional value weight map 304.

At 130, in the illustrated embodiment, the redistributed functional volumetric information is post-processed. For example, filtering may be applied. As another example, the redistributed functional volumetric information may be re-sampled for a desired visualization optimization. At 132, an image is generated using the redistributed functional volumetric data (which, in some embodiments, is post-processed at 130). At 134, the image is displayed (e.g. via a screen or printout). The image in various embodiments may display only the redistributed functional data, or may display one or more of the anatomical structures of the structural image or the original, non-redistributed functional data. As one example, the redistributed functional data may be displayed overlaid with the anatomical data on one portion of a screen, while the original, non-redistributed functional data is displayed on a different portion of a screen, allowing a user to compare redistributed and non-redistributed images.

Figure 3:
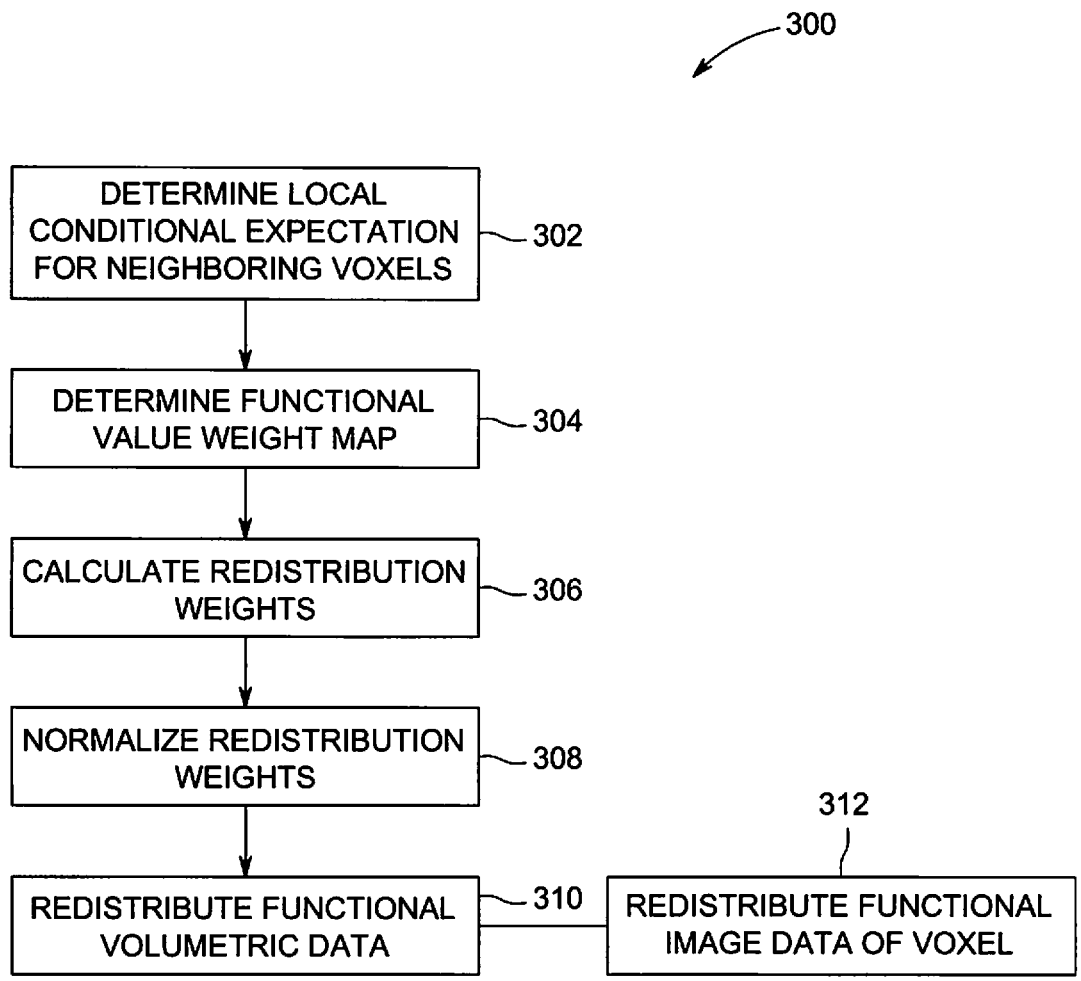
FIG. 3 is a flowchart of a method in accordance with various embodiments described herein.

FIG. 3 illustrates a flowchart of a method 300. It may be noted that one or more aspects of the method 300 may be performed in conjunction with the method 100, for example in connection with step 122 of the method 100. The operations of FIG. 3 may be implemented by one or more processors executing program instructions stored in memory. The method 300, for example, may employ structures or aspects of various embodiments (e.g., systems and/or methods) discussed herein, such as the system 500. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 300 may be used as one or more algorithms to direct hardware to perform one or more operations described herein. It should be noted, other methods may be used, in accordance with embodiments herein.

At 302, for each voxel of the functional volumetric data, a local conditional expectation set of values is determined for a plurality of neighboring voxels. For example, for each analyzed voxel, and each neighboring voxel of the analyzed voxel, a local conditional expectation value may be calculated based on the ratios corresponding to the functional image values and anatomical probability map values. The ratios accordingly correspond to a pair of voxels—the analyzed voxel and a neighboring voxel. In various embodiments, while processing an analyzed voxel and its neighborhood in their turn, a local conditional expectation value may be calculated for the analyzed voxel and each one of its defined neighboring voxels. Voxel pairs may be defined, with each neighboring voxel forming a voxel pair with the voxel being analyzed. For each pair of voxels, the expectation value may be based on the ratio between the two functional image values, and on the ratio between the two anatomical probability map values for the respective voxels of the voxel pair. Determining the conditional expectation value reassesses the assigned probability, not only on the pre-calculated value in the neighbor voxel, but also on the relative values of the functional image data in the voxels, thereby setting a new condition in the process. This approach in various embodiments beneficially helps preserve functional data concentrations which are actually outside, and not originated from the anatomical objects. Additional details of an example embodiment of determining a local conditional expectation are provided in connection with method 400 discussed herein. (See FIG. 4 and related discussion.)

At 304, a functional value weight map is determined. The functional value weight map is determined based on a function of the functional image values of a voxel being analyzed and a neighbor voxel. Use of such a functional value weight map in various embodiments may add a sharpening effect to functional-images, which may tend toward lower resolution. In some embodiments, the functional value weight map may be generated by a power function (e.g., ^X, where x is between 0.5 to 2.0) applied on the functional data.

At 306, a redistribution weight is calculated. For example, for each neighboring voxel of a voxel being analyzed, a redistribution weight may be calculated by multiplying several values. In the illustrated embodiment, the local conditional expectation value, the functional value weight of the neighboring voxel, and the proximity weight (which corresponds to a function of the distance from the analyzed voxel to the neighbor voxel (see, e.g., step 116 of method 100)) may be multiplied to provide the redistribution weight.

At 308, the redistribution weights are normalized. In the illustrated embodiment, after assigning the final redistribution weights at 306 to all neighbor voxels of the analyzed voxel, the group of weights (the weights for all of the neighbor voxels for a particular analyzed voxel) is normalized such that the sum of the weights for all of the neighbor voxels for the particular analyzed voxel equals 1.

At 310, the portion of the functional volumetric data to be redistributed is redistributed. The redistribution may be performed based on accumulated redistribution values of voxels of the functional volumetric data. For example, after the processing of each analyzed voxel, the resulting data may be appended to results from previously analyzed voxels. In the illustrated embodiment, at 312, functional image data of an analyzed voxel is redistributed. The functional image data is redistributed across its neighbor voxels. For example, for each neighbor voxel, a new value may be assigned by multiplying the analyzed voxel functional image value with the final redistribution weight of the neighbor voxel. The process at 312 may be repeated for each analyzed voxel, with the results accumulated and utilized at 310.

Figure 4:
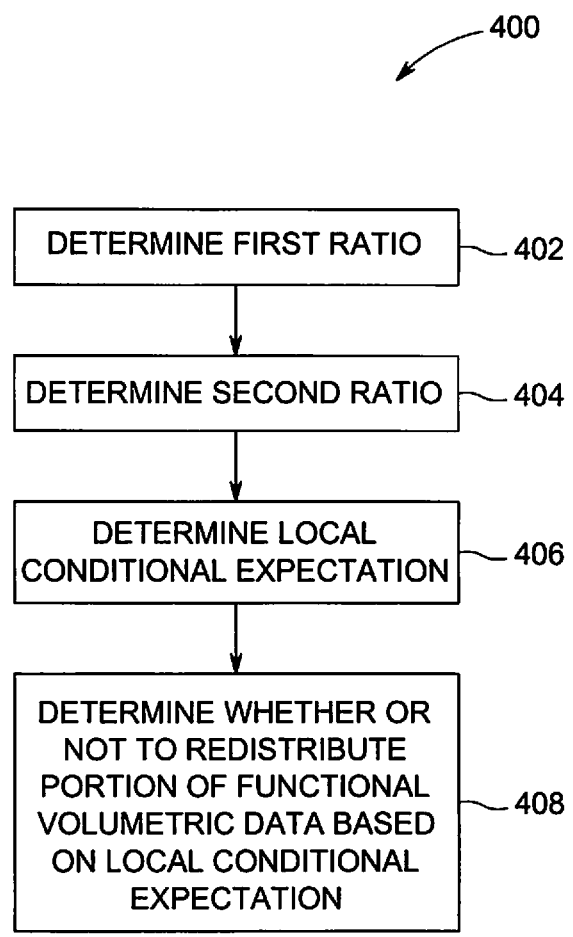
FIG. 4 is a flowchart of a method in accordance with various embodiments described herein.

FIG. 4 illustrates a flowchart of a method 400. It may be noted that one or more aspects of the method 400 may be performed in conjunction with the method 100 and/or the method 300, for example in connection with step 122 of the method 100 and/or step 302 of the method 300. The operations of FIG. 4 may be implemented by one or more processors executing program instructions stored in memory. The method 400, for example, may employ structures or aspects of various embodiments (e.g., systems and/or methods) discussed herein, such as the system 500. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 400 may be used as one or more algorithms to direct hardware to perform one or more operations described herein. It should be noted, other methods may be used, in accordance with embodiments herein.

At 402, a first ratio is determined. The first ratio is based on functional image data for a given voxel being analyzed and a neighboring voxel. (It may be noted that various aspects of FIG. 4 may be repeated for plural voxels to be analyzed, and/or for each neighbor of the voxels being analyzed). For example, the first ratio may be the ratio between the functional image values of the neighbor voxel and the analyzed voxel.

At 404, a second ratio is determined. The second ratio is determined based on values of the anatomical probability map (see FIG. 1 and related discussion) for the voxel being analyzed and the neighboring voxel. For example, the second ratio may be the ratio between the anatomical probability map values of the neighbor voxel and the voxel being analyzed.

At 406, a local conditional expectation is determined. In the depicted embodiment, the local conditional expectation is based on the two ratios determined at 402 and 404. Generally, the local conditional expectation indicates whether or not it is reasonable to directly assign the anatomical probability map value of the neighbor voxel to construct the redistribution weight between the voxel being analyzed and the neighbor voxel. For example, a series of conditions or joint conditions may be used to determine the local conditional expectation. In one example, a first condition is whether or not the first ratio is within a predetermined range (e.g., if the first ratio is less than 1). A second condition is whether or not the second ratio is within a predetermined range (e.g., if the second ratio is greater than 1). A third joint condition is whether the first condition result is the same as the second condition result (i.e., if both are true or both are false). Then, if the joint condition is met, the local conditional expectation is considered satisfied. However, if the joint condition is not met, then the local conditional expectation is not considered satisfied.

At 408, it is determined whether or not to redistribute a portion of the functional volumetric data corresponding to the voxel being analyzed and the neighbor voxel based on the local conditional expectation value. For example, if the local conditional expectation value is met, the anatomical probability map value of the analyzed voxel is assigned to construct the redistribution weight between the voxel being analyzed and the neighbor voxel. However, if the local conditional expectation value is not met, the anatomical probability map value of the neighbor voxel is assigned to construct the redistribution weight between the voxel being analyzed and the neighbor voxel.

To illustrate various aspects of the method 400, an example scenario may be considered. In the example scenario, a radiotracer may be administered to a patient to be imaged, with the radiotracer mainly targeted to bones. In the example scenario, a voxel being analyzed is on soft tissue, and a neighbor voxel is on bone. If the radiotracer activity is higher in the neighbor voxel, the probability map value of the bone will be taken for the redistribution process for the voxel pair, which helps to concentrate the activity in the neighbor voxel in this case. However, if the tracer activity is higher in the analyzed voxel (an anomaly where the activity is higher in the soft tissue than for the bone), the probability map value of the soft-tissue will be utilized for the redistribution process for the voxel pair, which helps to maintain the activity in the analyzed voxel in this case.

In a converse situation, the analyzed voxel is on bone and the neighbor voxel is on soft tissue. In this situation, if the tracer activity is higher in the neighbor voxel (an anomaly where the activity is higher in the soft tissue than for the bone), the probability map value of the bone will be utilized for the redistribution process for the voxel pair, which helps to maintain the activity in the neighbor voxel in this case. However, if the tracer activity is higher in the analyzed voxel (on bone), the soft-tissue probability will be taken, which helps to concentrate the activity in the analyzed voxel in this case. Note that, for the example scenario, according to the set conditions, in regular situations in which the analyzed voxel is on bone and the neighbor voxel is on soft tissue, and the tracer activity is higher in the analyzed voxel, the probability map value of the soft-tissue will be taken for the voxel pair, showing that high activity (or probability-map values) does not alone determine from which voxel the probability-map value will be taken.

It may be noted that other functions and/or logical conditions may be employed to redistribute functional data (e.g., determined which portions of functional data are to be redistributed and which portions are not) in various embodiments. For example, using the conditions discussed above, it may be determined that the first condition is equal to 1 where the first ratio is below a first threshold (e.g., 0.7) and that the first condition is equal to 0 when the first ratio is above a second threshold (e.g., 1.3). If neither threshold is satisfied (e.g., the first ratio is between 0.7 and 1.3), the probability map value may be weighted accordingly, between the two different values of the analyzed and neighbor voxels. Such an approach may provide a more smoothed or regulated conditional determination, helping to prevent sharp image-value transitions and potential image artifacts.

It may be noted that various processes discussed herein may be characterized as finite scale-dependent algorithmic processes. Accordingly, they may be suitable for execution in a multi-resolution approach, which may save processing time and better balance between structures with different ranges of spatial frequencies. For implementation with processing of two different scales (it may be noted that more scales are also possible), the process may be described as follows.

First, matching volumetric grids of functional and anatomical image volumes are obtained. Next, scale-independent range-related kernels are determined. For example, 3D Gaussian weights based on number of voxels (and not absolute distance) may be utilized. The redistribution process may then be performed using the first functional-anatomical volumes. Next, the functional-anatomical values may be down-sampled (e.g., by ½ in each dimensions). After the down-sampling, the redistribution process may be performed on the down-sampled functional-anatomical values, using the same kernels. The first redistributed functional data may be down-sampled, and the down-sampled first redistributed functional data may be subtracted from the redistributed down-sampled data. The resulting difference may next be up-sampled, and added to the first redistributed data. In such a multi-resolution approach, the determined kernels may be much smaller (e.g., less voxels to process) than the kernel size for a single resolution processing.

Figure 5:
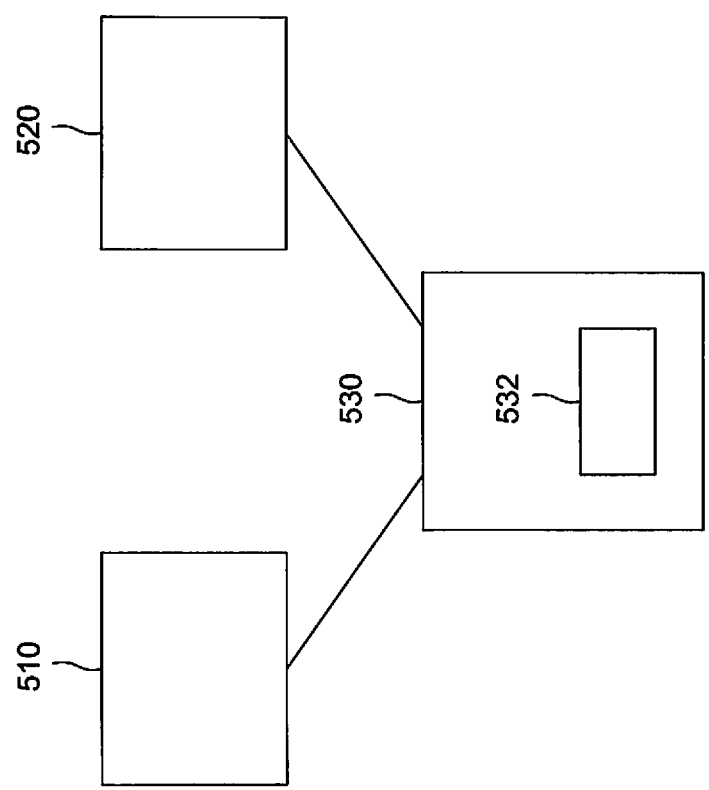
FIG. 5 is a schematic block diagram illustrating a system in accordance with various embodiments described herein.

FIG. 5 illustrates a system 500 formed in accordance with various embodiments. As seen in FIG. 1, the system 500 includes a structural imaging acquisition unit 510, a functional imaging acquisition unit 520, and a processing unit 530. Generally, the structural imaging acquisition unit 510 is configured to perform a scan to acquire structural or anatomical imaging information, and the functional imaging acquisition unit 520 is configured to perform a scan to acquire functional imaging information. The structural imaging acquisition unit 510, for example, may be configured to perform one or more of X-ray, CT, MRI, or US scans. The functional imaging acquisition unit 520, for example, may be configured to perform one or more of PET or SPECT scans. It may be noted that the structural imaging acquisition unit 510 and the functional imaging acquisition unit 520 may be part of a single installation, or multi-modality imaging system.

The processing unit 530 may be located remotely from the imaging acquisition units, or in the same location. Generally, the processing unit 530 is configured to obtain a structural image including anatomical volumetric data. For example, the structural image may be obtained by reconstructing an image using the structural imaging information acquired by the structural imaging acquisition unit 510 (or obtaining such an image that has already been reconstructed. Also, the processing unit 530 is configured to obtain a functional image including functional volumetric data. For example, the functional image may be obtained by reconstructing an image using the functional imaging information acquired by the functional imaging acquisition unit 520 (or obtaining such an image that has already been reconstructed). The depicted processing unit 530 is also configured to determine an anatomical probability map corresponding to a probability that a determined anatomical object correlates to potential functional data, and to redistribute the functional volumetric data using the anatomical probability map to provide redistributed functional volumetric data. For example, the depicted processing unit 530 in various embodiments is configured to perform one or more aspects of methods 100, 300, 400 discussed herein. Further, the processing unit 530 may include or be coupled to a display that may be used to display an image generated by the processing unit 530 using the re-distributed volumetric data.

The depicted processing unit 530 includes a memory 532. The processing unit 530 is depicted as including a single processing unit 530; however, the block for the processing unit 530 may be understood as representing one or more processors that may, in some embodiments, be distributed or remote from each other.

The processing unit 530 may include processing circuitry configured to perform one or more tasks, functions, or steps discussed herein. It may be noted that "processing unit" as used herein is not intended to necessarily be limited to a single processor or computer. For example, the processing unit 530 may include multiple processors and/or computers, which may be integrated in a common housing or unit, or which may distributed among various units or housings.

Generally, various aspects (e.g., programmed modules) of the processing unit 530 act individually or cooperatively with other aspects to perform one or more aspects of the methods, steps, or processes discussed herein (e.g., methods 100, 300, 400, or aspects thereof). In the depicted embodiment, the memory 532 includes a tangible, non-transitory computer readable medium having stored thereon instructions for performing one or more aspects of the methods, steps, or processes discussed herein. It may be noted other aspects of the system 500 (e.g., the acquisition units) may include similar processing units (e.g., including at least one processor and associated memory configured to act individually or cooperatively with other aspects to perform one or more aspects of the methods, steps, or processes discussed herein).

Figure 6:
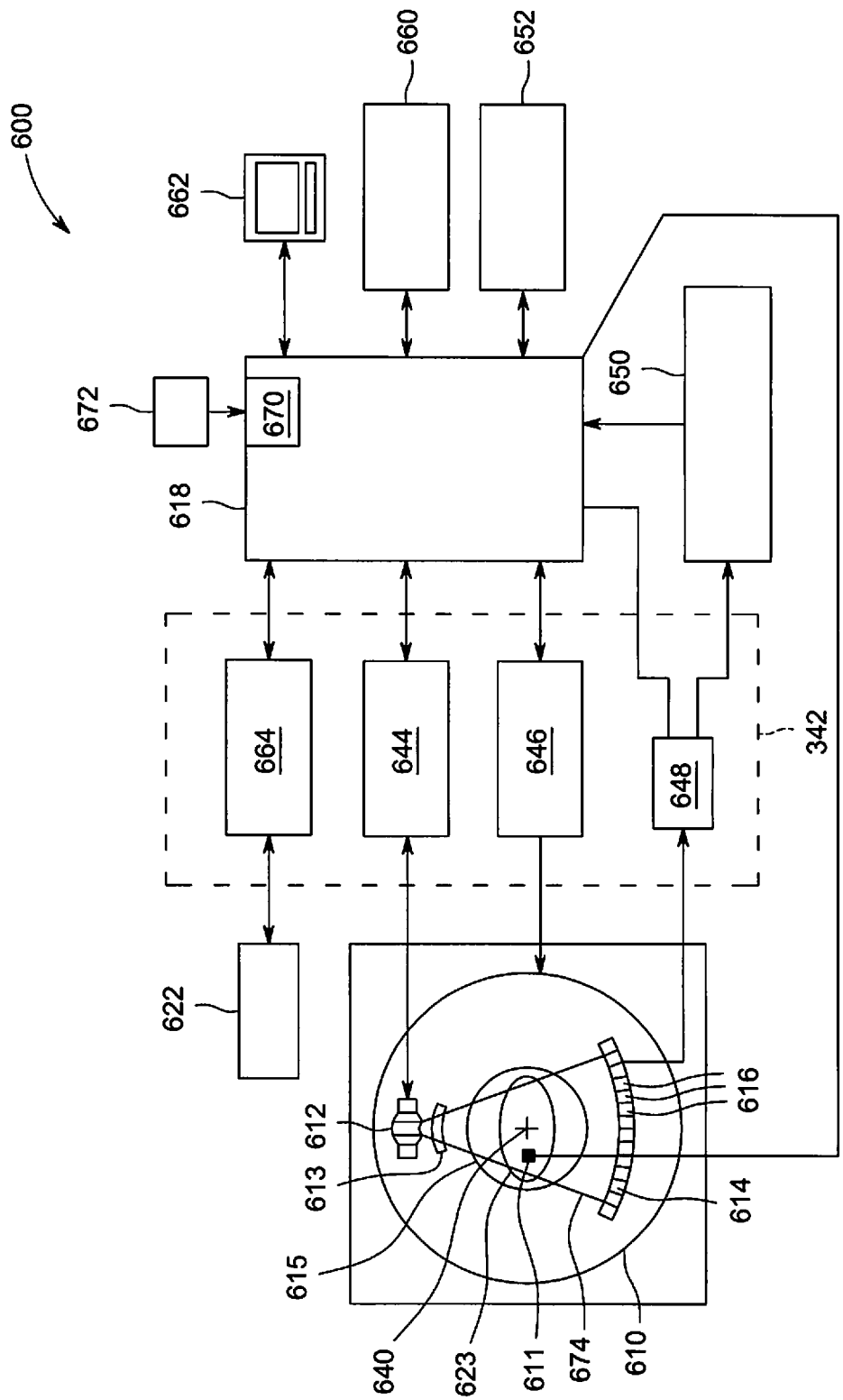
FIG. 6 is a schematic block diagram illustrating an imaging system in accordance with various embodiments described herein.

FIG. 6 illustrates a schematic diagram of an exemplary CT imaging system 600 that may be utilized to implement various embodiments discussed herein (e.g., as all or a portion of the structural imaging acquisition unit 510). Although the CT imaging system 600 is illustrated as a standalone imaging system, it should be noted that the CT imaging system 600 may form part of a multi-modality imaging system in some embodiments. For example, the multi-modality imaging system may include the CT imaging system 600 and a positron emission tomography (PET) imaging system, or a single photon emission computed tomography (SPECT) imaging system. It should also be noted that in various embodiments one or more imaging modalities other than CT may be employed. It should also be understood that other imaging systems capable of performing the functions described herein are contemplated as being used.

The CT imaging system 600 includes a gantry 610 that has the X-ray source 612 that projects a beam of X-rays toward the detector array 614 on the opposite side of the gantry 610. A source collimator 613 and a bowtie filter module (not shown) are provided proximate the X-ray source 612. The detector array 614 includes a plurality of detector elements 616 that are arranged in rows and channels that together sense the projected X-rays that pass through a patient 623 (e.g., object of interest). The imaging system 600 may include a physiologic sensor 611 (e.g., electrocardiogram (ECG), a respiratory sensor) proximate to the patient 623 for cardiac or respiratory gating.

A motorized table 622 is utilized to move the patient 623 into and out of the gantry 610 at a table feed rate. Particularly, the table 622 moves at least a portion of the patient 623 through a gantry opening 615 along a z-axis that extends through the gantry 610. Further, the table 622 may be used to move the patient 623 vertically within the bore of the gantry 610.

The depicted detector array 614 includes a plurality of detector elements 616. Each detector element 616 produces an electrical signal, or output, that represents the intensity of an impinging X-ray beam and hence allows estimation of the attenuation of the beam as it passes through the patient 623. During a scan to acquire the X-ray projection data, the gantry 610 and the components mounted thereon rotate about a center of rotation 640. FIG. 6 shows only a single row of detector elements 616 (i.e., a detector row). However, the multi-slice detector array 614 includes a plurality of parallel detector rows of detector elements 616 such that projection data corresponding to a plurality of slices can be acquired simultaneously during a scan.

In the exemplary embodiment, the X-ray source 612 and the detector array 614 are rotated with the gantry 610 within the imaging plane and around the patient 623 to be imaged such that the angle at which an X-ray beam 674 intersects the patient 623 constantly changes. A group of X-ray attenuation measurements, i.e., projection data, from the detector array 614 at one gantry angle is referred to as a "view" or "projection." A "scan" of the patient 623 comprises a set of views made at different gantry angles, or view angles, during one or more revolutions of the X-ray source 612 and the detector array 614. In a CT scan, the projection data is processed to reconstruct an image that corresponds to a three-dimensional volume taken of the patient 623. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

Rotation of the gantry 610, the operation of the X-ray source 612, and position of the motorized table 622 are governed by an acquisition subsystem 642 based on one or more scan settings (e.g., tube current/voltage, focal spot size, duty cycle, kV pair, rotation speed, collimation width, field of view size, body dose, exposure time, head dose, helical pitch) defined by a scan prescription or protocol. The acquisition subsystem 642 includes an X-ray controller 644 that provides power and timing signals to the X-ray source 612 based on the scan settings defined by the scan prescription or protocol. The X-ray controller 644 may deliver power (e.g., tube current, tube voltage) and/or configure the X-ray source 612 to project X-rays having a certain field of view and/or collimation width (e.g., collimation slab) based on the scan settings defined by the scan prescription or protocol. Additionally or alternatively, the X-ray controller 644 may control a focal spot size of the X-ray source 612 based on the scan settings defined by the scan prescription or protocol. Optionally, for dual-energy CT scans, the X-ray controller 644 may define the dual energy levels (e.g., kV pair) and duty cycle of the X-rays emitted by the X-ray source 612.

The acquisition subsystem 642 also includes a gantry motor controller 646 that controls the rotational speed and position of the gantry 610. For example, the gantry motor controller 346 may rotate the gantry 610 at a rotational velocity based on the scan settings defined by the scan prescription or protocol.

In addition, the acquisition subsystem 642 may also include a table motor controller 664 that controls the motorized table 622 to position the patient 623 in the gantry 610 based on the scan settings defined by the scan prescription or protocol. Particularly, the motorized table 622 moves at least a portion of the patient 623 through the gantry opening at a table feed rate.

The scan prescription or protocol may be stored on a storage device 652 which is communicatively coupled to the acquisition subsystem 642. The storage device 652 may be a tangible and non-transitory computer readable medium such as flash memory, RAM, ROM, EEPROM, and/or the like. The scan prescription or protocol may be defined by a processing unit 318.

The processing unit 618 may include one or more processors. Optionally, the processing unit 618 may include a central controller circuit (CPU), one or more microprocessors, a graphics controller circuit (GPU), or any other electronic component capable of processing inputted data according to specific logical instructions. Additionally or alternatively, the processing unit 618 may execute instructions stored on a tangible and non-transitory computer readable medium (e.g., the storage device 652, integrated memory of the processing unit 618). The processing unit 618 receives the projection data from the detector array 614 and processes the projection data to reconstruct an image of the patient 623.

The processing unit 618 is operably coupled to a display 662 and the user interface 660. The display 662 may include one or more liquid crystal displays (e.g., light emitting diode (LED) backlight), organic light emitting diode (OLED) displays, plasma displays, CRT displays, and/or the like. The display 662 allows the operator to observe the reconstructed image and other data generated by the processing unit 618. For example, the display 662 may display patient information, one or more CT images, components of a display interface, measurements, diagnosis, treatment information, and/or the like.

The user interface 660 controls operations of the CT imaging system 600 and is configured to receive inputs (e.g., CID) from the user. The user interface 660 may include a keyboard, a mouse, a touchpad, one or more physical buttons, and/or the like. Optionally, the display 662 may be a touch screen display, which includes at least a portion of the user interface 642. For example, the user may select one or more user selectable elements shown on the display by touching or making contact with touch sensitive portions of the display 662.

A data acquisition system (DAS) 648 in the acquisition subsystem 642 samples analog data from detector elements 616 and converts the data to digital signals, the projection data, for subsequent processing. An image reconstructor circuit 650 receives the projection data from the DAS 648 and performs an image reconstruction. The image reconstructor circuit 650 may include one or more processors, field programmable arrays, one or more ASICs, a CPU, or any other electronic component capable of processing inputted data according to specific logical instructions. Additionally or alternatively, the image reconstructor circuit 650 may execute programmed instructions stored on a tangible and non-transitory computer readable medium (e.g., the storage device 652, integrated memory of the image reconstructor circuit 650). For example, the one or more processors may perform one or more operations by executing programmed instructions stored on the storage device 652 and/or integrated memory such as EEPROM. The image reconstructor circuit 650 may generate the resultant medical image based on reconstructed settings received via the user interface 660 and/or based on the scan attributes. The reconstruction settings may include select keV energy level(s), iterative reconstruction (e.g., adaptive statistical reconstruction), direct multi-planar reconstruction, algorithmic reconstruction, and/or the like.

The projection data is processed by the image reconstructor circuit 650 to reconstruct resultant medical images that corresponds to a two dimensional (2D) slice taken through the patient 623. In some embodiments, a 3D reconstruction may be reconstructed directly. The image reconstructor circuit 350 may convert the attenuation measurements associated with the projection data into a medical image of the patient 623. The attenuation measurements are typically converted into units of "CT numbers" or Hounsfield units (HU). The image is represented as a matrix of numbers, with each individual number in the image matrix representing a three-dimensional (3D) volume element in the scanned part, called a "voxel." To obtain a visual image, each voxel is represented as a 2D picture element, or "pixel." Each pixel has a shade of gray based on the HU value representing the attenuation measurement within the corresponding voxel. For example, the HU value may correspond to a brightness of each pixel such that a pixel having a higher HU value may be brighter relative to a pixel having a lower HU value. The reconstructed medical images generated by the image reconstructor circuit 650 are input to the processing unit 618 that stores the image in the storage device 652. Optionally, the image reconstructor circuit 650 may be integrated with and/or similar operations may be performed by the processing unit 618.

Additionally or alternatively, the processing unit 618 includes a device 670, for example, a CD-ROM drive, DVD drive, magnetic optical disk (MOD) device, and/or any other digital device including a network connecting device such as an Ethernet device for reading instructions and/or data from a tangible non-transitory computer-readable medium 672.

Figure 7:
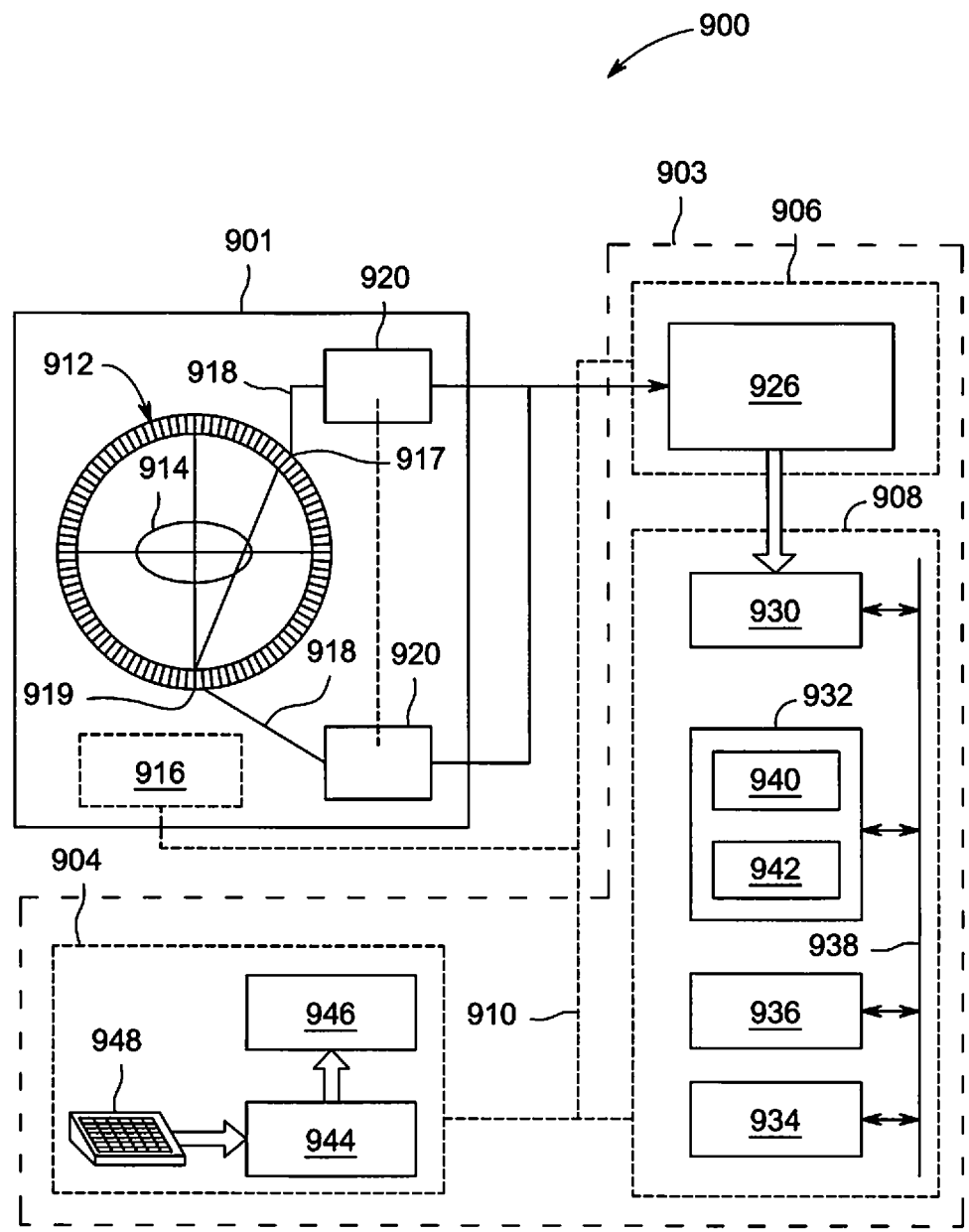
FIG. 7 is a schematic block diagram illustrating an imaging system in accordance with various embodiments described herein.

FIG. 7 is a block diagram of an exemplary embodiment of a PET system 900 in which various embodiments may be implemented. The PET system 900, for example, may form all or a portion of the functional imaging acquisition unit 520. The PET system 900 includes a PET scanner 901 and a controller 903 to control image reconstruction processes. The controller 903 includes an operator workstation 904 and a processor 905. The processor 905 includes a data acquisition processor 906 and an image reconstruction processor 908. The PET scanner 901, operator workstation 904, data acquisition processor 906 and image reconstruction processor 908 are interconnected via a communication link 910 (e.g., a serial communication or wireless link). The PET scanner 901, which typically includes a gantry (not shown in FIG. 7), acquires scan data and transmits the data to the data acquisition processor 906. The operation of the PET scanner 901 is controlled from operator workstation 904. The data acquired by data acquisition processor 906 is reconstructed using image reconstruction processor 908.

The PET scanner 901 may operate, using, for example, a plurality of detector rings. One such detector ring, detector ring 912, is illustrated in FIG. 7, which includes detector elements formed in accordance with various embodiments. In various embodiments, the detector elements may include one or more of scintillators, tube photo-multipliers or Silicon photo-multipliers. The detector ring 912 includes a central opening, in which an object 914 (e.g., a patient) may be positioned, using, for example, a motorized table that is aligned with the central axis of the ring 912. The motorized table moves the object 914 into the central opening of the ring 912, in response to one or more commands received from operator workstation 904. A PET scanner controller 916, also referred to as a gantry controller, is provided (e.g., mounted) in the PET scanner 901. The PET scanner controller 916 responds to the commands received from the operator workstation 904 through the communication link 910. Therefore, the operation of the PET scanner 901 is controlled from the operator workstation 904 through the PET scanner controller 916.

The detector ring 912 includes a plurality of detector elements for performing a PET scan of the object 914. For example, there may be 420 crystals per ring and 24 rings in the scanner. As shown in FIG. 10, the detector ring 912 includes a first detector element 917, a second detector element 919, and several other detectors. It should be noted that the detector elements are referred to as the first detector element and the second detector element, only to differentiate location in FIG. 7. The first detector element 917, like the other detectors, includes a set of scintillator crystals arranged in a matrix that is disposed in front of a plurality of photosensors. When an annihilation photon impinges on a crystal on a detector, the annihilation photon produces a scintillation in the crystal. Each photosensor produces an analog or digital signal on the communication line 918 when a scintillation event occurs. A set of acquisition circuits 920 is provided within the PET scanner 901 to receive these analog or digital signals. The acquisition circuits 920 may include analog-to-digital converters to digitize analog signals, processing electronics to quantify event signals and a time measurement unit to determine time of events relative to other events in the system. For example, this information indicates when the event took place and the identity of the scintillation crystal that detected the event. The acquisition circuits produce digital data indicating the location, time and total energy of the event. This event data is transmitted through a communication link, for example, a cable, to a coincidence detector or processor 926.

The coincidence detector 926 receives the event data packets from the acquisition circuits 920 and determines if any two of the detected events are in coincidence. In this context, the coincidence is determined by a number of factors. First, the time markers in each event data packet must be within a predetermined time period, for example, 6 ns, of each other. Secondly, the LOR formed by a straight line joining the two detectors that detect the coincidence event should pass through the field of view in PET scanner 901. Events that cannot be paired are discarded. Coincident event pairs are recorded as a coincidence data packet that is communicated through a communication link to a sorter 930 in the image reconstruction processor 908.

The image reconstruction processor 908 includes the sorter 930, a memory module 932, an image CPU 934, an array processor 936, and a back-plane bus 938. The sorter 930 counts all events that occur along each projection ray and organizes them into a coincidence data set. In one embodiment, this data set is organized as a data array 940, referred to as a sinogram. The data array 940 is stored in the memory module 932. The back-plane bus 938 is linked to the communication link 910 through the image CPU 934, which controls communication through the back-plane bus 938. The array processor 936 is also connected to the back-plane bus 938, receives the data array 940 as an input, and reconstructs images in the form of the image arrays 942. The resulting image arrays 942 are stored in the memory module 932.

The images stored in the image array 942 are communicated by the image CPU 934 to the operator workstation 904. The operator workstation 904 includes a CPU 944, a display device 946, and an input device 948. The CPU 944 connects to the communication link 910 and receives inputs (e.g., user commands) from the input device 948, which may be, for example, a keyboard, mouse, or a touch-screen panel. The operator can control the calibration of the PET scanner 901, the configuration of the PET scanner 901, and the positioning of the object 914 for a scan through the input device 948 and associated control panel switches. Similarly, the operator can also control the display of the resulting image on the display device 946 and perform image-enhancement functions, using programs executed by the workstation CPU 944.

The processor 905 is configured to process the scan data received from the detector elements. The scan data includes, for example, sinogram and timing information that is received by processor 905 from the detector elements during an imaging scan. The timing information in one embodiment is the difference in time at which two annihilation photons emitted in an annihilation event are detected by detector elements. The timing information may include time stamp information relating to a measured annihilation event detected by a pair of detector elements, for example, the first detector element 917 and the second detector element 919, for the PET system 900. The time stamp information is the time at which each annihilation photon is detected by a detector element, which in various embodiments.

The timing information is received by detectors, which include, for example, a block of 36 scintillator crystals attached to an array of photosensors. The scintillator crystals convert the incoming annihilation photon from the patient into a plurality (e.g., several thousand) of light photons (e.g., visible or near UV), which are detected by the photosensors. The proportion of light photons detected by each photosensor channel is used to determine which of the 36 crystals received the incoming photon. The timing signal is determined by processing the leading edge of the signals, to estimate the arrival of the light photons at the light sensors 34 of, for example, the SIPM. This timing signal is then digitized and processed subsequently.

The energy and timing information are used to reconstruct an image of the object 914, scanned by the PET system 900. The reconstruction may include, for example, a two-dimensional or three-dimensional reconstruction. The timing data of each detector element may be configured as a timing bias matrix with a timing recovery value for each set of projection rays of the PET system 900. It should be noted that a detector element pair detects the projection rays from an annihilation event. The timing bias data of each detector element pair corresponding to the projection ray is stored in the memory module 932 of the PET system 900.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "processing unit," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:
1. A system comprising:
   a structural imaging acquisition unit configured to perform a structural scan to acquire structural imaging information of a patient;
   a functional imaging acquisition unit configured to perform a functional scan to acquire functional imaging information of a patient;
   one or more processors configured to:
      obtain, using the structural imaging information, a structural image of the patient including anatomical volumetric data;

determine an anatomical probability map corresponding to a probability that a determined anatomical object correlates to potential functional data;

obtain, using the functional imaging information, a functional image of the patient including functional volumetric data;

re-distribute the functional volumetric data using the anatomical probability map to provide re-distributed functional volumetric data; and generate an image using the re-distributed functional volumetric data.

2. The system of claim 1, wherein the one or more processors are configured to:

determine if one or more portions of the functional volumetric data corresponds to an anatomical structure using the anatomical probability map;

if the one or more portions of the functional volumetric data corresponds to the anatomical structure, re-distribute the one or more portions of the functional volumetric data to correlate with one or more portions of the anatomical volumetric data corresponding to the anatomical structure; and if the one or more portions of the functional volumetric data do not correspond to the anatomical structure, to not re-distribute the one or more portions of the functional volumetric data.

3. The system of claim 1, wherein the one or more processors are configured to:

determine a first ratio based on functional image data for a given voxel and a neighboring voxel;

determine a second ratio based on values of the anatomical probability map for the given voxel and the neighboring voxel;

determine a local conditional expectation value based on the first and second ratios; and determine whether or not to re-distribute a portion of the functional volumetric data corresponding to the voxels based on the local conditional expectation value.

4. The system of claim 3, wherein the first ratio is a ratio between functional image values of the neighboring voxel and the given voxel, wherein the second ratio is a ratio between anatomical probability map values of the neighboring voxel and the given voxel, wherein the local conditional expectation value is met when the first ratio is less than one and the second ratio is greater than one, or when the first ratio is greater than one and the second ratio is less than one; and when the local conditional expectation is met, the one or more processors are configured to assign the anatomical probability map value of the given voxel to a re-distribution corresponding to the voxels.

5. The system of claim 1, wherein the one or more processors are configured, for each voxel of the functional volumetric data, to:

determine the local conditional expectation for the plurality of neighboring voxels;

calculate a re-distribution weight for each neighboring voxel;

normalize the calculated re-distribution weights; and re-distribute the portion of the functional volumetric data based on accumulated redistribution values of the voxels of the functional volumetric data.

6. The system of claim 5, wherein the one or more processors are configured, for each voxel of the functional volumetric data, to:

determine a functional-value weight map based on a function of the functional image values of the given voxel and the neighboring voxel; and calculate the re-distribution weight for each neighboring voxel by multiplying the local conditional expectation value, the functional-value weight of the neighboring voxel from the functional-value weight map, and a proximity weight corresponding to a proximity of the neighboring voxel to the given voxel.

7. The system of claim 1, wherein the structural imaging acquisition unit comprises at least one of a computed tomography (CT) acquisition unit or a magnetic resonance imaging (MRI) unit.

8. The system of claim 1, wherein the functional imaging acquisition unit comprises at least one of a positron emission tomography (PET) acquisition unit or a single photon emission computed tomography (SPECT) acquisition unit.

9. A method comprising:

obtaining a structural image of the patient including anatomical volumetric data;

determining an anatomical probability map corresponding to a probability that a determined anatomical object correlates to potential functional data;

obtaining a functional image of the patient including functional volumetric data;

re-distributing the functional volumetric data using the anatomical probability map to provide re-distributed functional volumetric data; and generating an image using the re-distributed functional volumetric data.

10. The method of claim 9, further comprising:

determining if one or more portions of the functional volumetric data corresponds to an anatomical structure using the anatomical probability map;

if the one or more portions of the functional volumetric data corresponds to the anatomical structure, re-distributing the one or more portions of the functional volumetric data to correlate with one or more portions of the anatomical volumetric data corresponding to the anatomical structure; and if the one or more portions of the functional volumetric data do not correspond to the anatomical structure, not re-distributing the one or more portions of the functional volumetric data.

11. The method of claim 9, further comprising:

determining a first ratio based on functional image data for a given voxel and a neighboring voxel;

determining a second ratio based on values of the anatomical probability map for the given voxel and the neighboring voxel;

determining a local conditional expectation value based on the first and second ratios; and determining whether or not to re-distribute a portion of the functional volumetric data corresponding to the voxel based on the local conditional expectation value.

12. The method of claim 11, wherein the first ratio is a ratio between functional image values of the neighboring voxel and the given voxel, wherein the second ratio is a ratio between anatomical probability map values of the neighboring voxel and the given voxel, wherein the local conditional expectation value is met when the first ratio is less than one and the second ratio is greater than one, or when the first ratio is greater than one and the second ratio is less than one; and when the local conditional expectation is met, the method further comprises assigning the anatomical probability map value of the given voxel to a re-distribution corresponding to the voxels.

13. The method of claim 9, further comprising, for each voxel of the functional volumetric data:
   determining the local conditional expectation for the plurality of neighboring voxels;
   calculating a re-distribution weight for each neighboring voxel;
   normalizing the calculated re-distribution weights; and
   re-distributing the one or more portions based on accumulated redistribution values of the voxels of the functional volumetric data.

14. The method of claim 13, further comprising, for each voxel:
   determining a functional-value weight map based on a function of the functional image values of the given voxel and the neighboring voxel; and
   calculating the re-distribution weight for each neighboring voxel by multiplying the local conditional expectation value, the functional-value weight of the neighboring voxel from the functional-value weight map, and a proximity weight corresponding to a proximity of the neighboring voxel to the given voxel.

15. A tangible and non-transitory computer readable medium comprising one or more computer software modules configured to direct one or more processors to:
   obtain a structural image of the patient including anatomical volumetric data;
   determine an anatomical probability map corresponding to a probability that a determined anatomical object correlates to potential functional data;
   obtain a functional image of the patient including functional volumetric data;
   re-distribute the functional volumetric data using the anatomical probability map to provide re-distributed functional volumetric data; and
   generate an image using the re-distributed functional volumetric data.

16. The tangible and non-transitory computer readable medium of claim 15, wherein the one or more computer software modules are further configured to direct the one or more processors to:
   determine if one or more portions of the functional volumetric data corresponds to an anatomical structure using the anatomical probability map;
   if the one or more portions of the functional volumetric data corresponds to the anatomical structure, re-distribute the one or more portions of the functional volumetric data to correlate with one or more portions of the anatomical volumetric data corresponding to the anatomical structure; and
   if the one or more portions of the functional volumetric data do not correspond to the anatomical structure, do not re-distribute the one or more portions of the functional volumetric data.

17. The tangible and non-transitory computer readable medium of claim 15, wherein the one or more computer software modules are further configured to direct the one or more processors to:
   determine a first ratio based on functional image data for a given voxel and a neighboring voxel;
   determine a second ratio based on values of the anatomical probability map for the given voxel and the neighboring voxel;
   determine a local conditional expectation value based on the first and second ratios; and
   determine whether or not to re-distribute a portion of the functional volumetric data corresponding to the voxel based on the local conditional expectation value.

18. The tangible and non-transitory computer readable medium of claim 17, wherein the first ratio is a ratio between functional image values of the neighboring voxel and the given voxel, wherein the second ratio is a ratio between anatomical probability map values of the neighboring voxel and the given voxel, wherein the local conditional expectation value is met when the first ratio is less than one and the second ratio is greater than one, or when the first ratio is greater than one and the second ratio is less than one; and
   when the local conditional expectation is met, the one or more computer software modules are further configured to direct the one or more processors to assign the anatomical probability map value of the given voxel to a re-distribution corresponding to the voxels.

19. The tangible and non-transitory computer readable medium of claim 15, wherein the one or more computer software modules are further configured to direct the one or more processors to, for each voxel of the functional volumetric data:
   determine the local conditional expectation for the plurality of neighboring voxels;
   calculate a re-distribution weight for each neighboring voxel;
   normalize the calculated re-distribution weights; and
   re-distribute the one or more portions based on accumulated redistribution values of the voxels of the functional volumetric data.

20. The tangible and non-transitory computer readable medium of claim 19, wherein the one or more computer software modules are further configured to direct the one or more processors to, for each voxel:
   determine a functional-value weight map based on a function of the functional image values of the given voxel and the neighboring voxel; and
   calculate the re-distribution weight for each neighboring voxel by multiplying the local conditional expectation value, the functional-value weight of the neighboring voxel from the functional-value weight map, and a proximity weight corresponding to a proximity of the neighboring voxel to the given voxel.

* * * * *